US00PP28310P3

(12) United States Plant Patent
Franco

(10) Patent No.: US PP28,310 P3
(45) Date of Patent: Aug. 22, 2017

(54) ***FRAGARIA* PLANT NAMED 'MALGA'**

(50) Latin Name: *Fragaria ananassa*
Varietal Denomination: MALGA

(71) Applicant: Zenti Franco, Verona (IT)

(72) Inventor: Zenti Franco, Verona (IT)

(73) Assignee: New Fruits SAS (IT)

( * ) Notice: Subject to any disclaimer, the term of this patent is extended or adjusted under 35 U.S.C. 154(b) by 56 days.

(21) Appl. No.: 14/545,788

(22) Filed: Jun. 19, 2015

(65) Prior Publication Data

US 2016/0374239 P1 Dec. 22, 2016

(51) Int. Cl.
*A01H 5/08* (2006.01)

(52) U.S. Cl.
USPC ..... Plt./209

(58) Field of Classification Search
USPC ..... Plt./209, 208
See application file for complete search history.

*Primary Examiner* — Anne Grunberg
(74) *Attorney, Agent, or Firm* — Cassandra Bright

(57) ABSTRACT

A new and distinct *Fragaria* plant named 'MALGA' is disclosed, characterized by consistent production of bright red, long conical fruit with a very good flavor and medium consistency. Plants are day neutral and have a high yield of fruit per plant. The new variety is a *Fragaria*, normally produced as an outdoor garden or container plant.

5 Drawing Sheets

Figure 1:
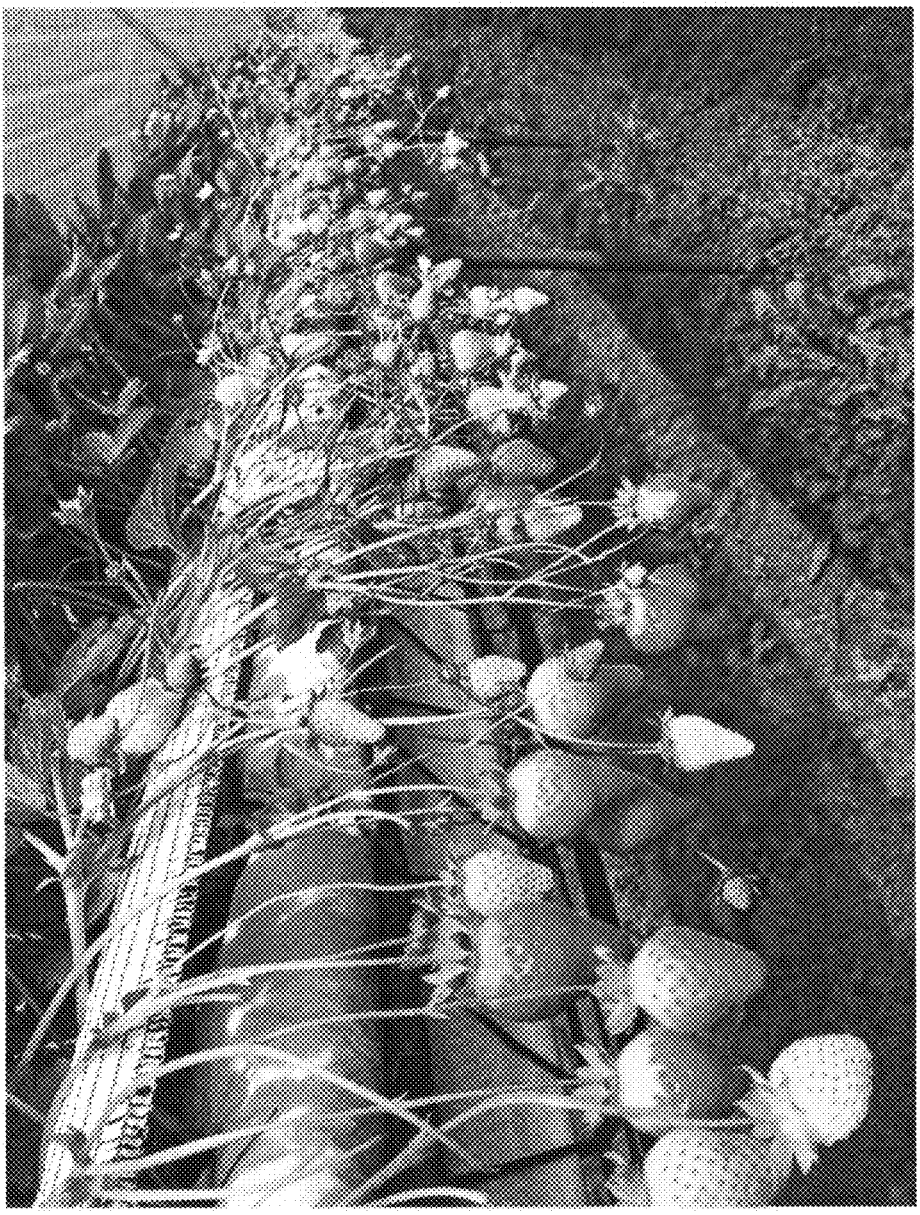

Latin name of the genus and species: *Fragaria ananassa.*
Variety denomination: 'MALGA'.

BACKGROUND OF THE INVENTION

The new *Fragaria* cultivar is a product of a planned breeding program conducted by the inventor, Zenti Franco, in Verona, Italy. The objective of the breeding program was to produce new *Fragaria* varieties for commercial applications. The cross resulting in this new variety was made during 2008.

The seed parent is the unpatented *Fragaria* 'Irma'. The pollen parent is the unpatented, propriety variety referred to as *Fragaria* 'SG8'. The new variety was selected during 2011 by the inventor in a group of seedlings resulting from the 2008 crossing in a research greenhouse in Verona, Italy.

Asexual reproduction of the new cultivar was first performed by vegetative runners. This was first performed at a research greenhouse in Verona, Italy in Summer of 2011. Subsequent propagation has shown that the unique features of this cultivar are stable and reproduced true to type in multiple successive generations.

SUMMARY OF THE INVENTION

The cultivar 'MALGA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MALGA'. These characteristics in combination distinguish 'MALGA' as a new and distinct *Fragaria* cultivar:

1. Bright red fruit color.
2. Long, conical shape of fruit. Very good flavor and medium consistency
3. Fruit with a good flavor and medium consistency.

4. Day length neutral variety.
5. High Productivity/Yield per plant.

Plants of the new cultivar 'MALGA' are similar to plants of the seed parent, *Fragaria* 'Irma' in most horticultural characteristics, however, plants of the new cultivar 'MALGA' differ in the following;

1. Plants of 'MALGA' produce significantly brighter red fruits.
2. The new variety has an improved fruit flavor.
3. Fruit of 'MALGA' is of more consistent size and shape.
4. The new variety produces slightly less fruit per plant than the seed parent.
5. The new variety exhibits better resistance to disease than the seed parent.

Plants of the new cultivar 'MALGA' are similar to plants of the pollen parent, *Fragaria* 'SG8' in most horticultural characteristics, however, plants of the new cultivar 'MALGA' differ in the following;

1. Plants of 'MALGA' produce more fruit per plant than the pollen parent.
2. Plants of 'MALGA' re-flower in greater quantity and more consistently than the pollen parent.

COMMERCIAL COMPARISON

Plants of the new cultivar 'MALGA' are comparable to the patented commercial variety *Fragaria* 'Portola' U.S. Plant Pat. No. 20,552. The two *Fragaria* varieties are similar in most horticultural characteristics; however, the new variety 'MALGA' differs in the following:

1. The new variety produces consistently larger fruit than 'Portola'.
2. The new variety produces fruit with a better flavor than 'Portola'.
3. The new variety produces fruit which is brighter red than 'Portola'.

BRIEF DESCRIPTION OF THE PHOTOGRAPHS

This new *Fragaria* is illustrated by the accompanying photographs which show the plant's form, foliage and inflorescences. The colors shown are as true as can be reasonably obtained by conventional photographic procedures. The photographs were taken using conventional techniques and although colors may appear different from actual colors cited due to faults caused by conventional photographic techniques.

FIG. 1: illustrates in full color typical fruiting plants of 'MALGA'. Age of the plants photographed is approximately 6 to 8 months.

Figure 2:
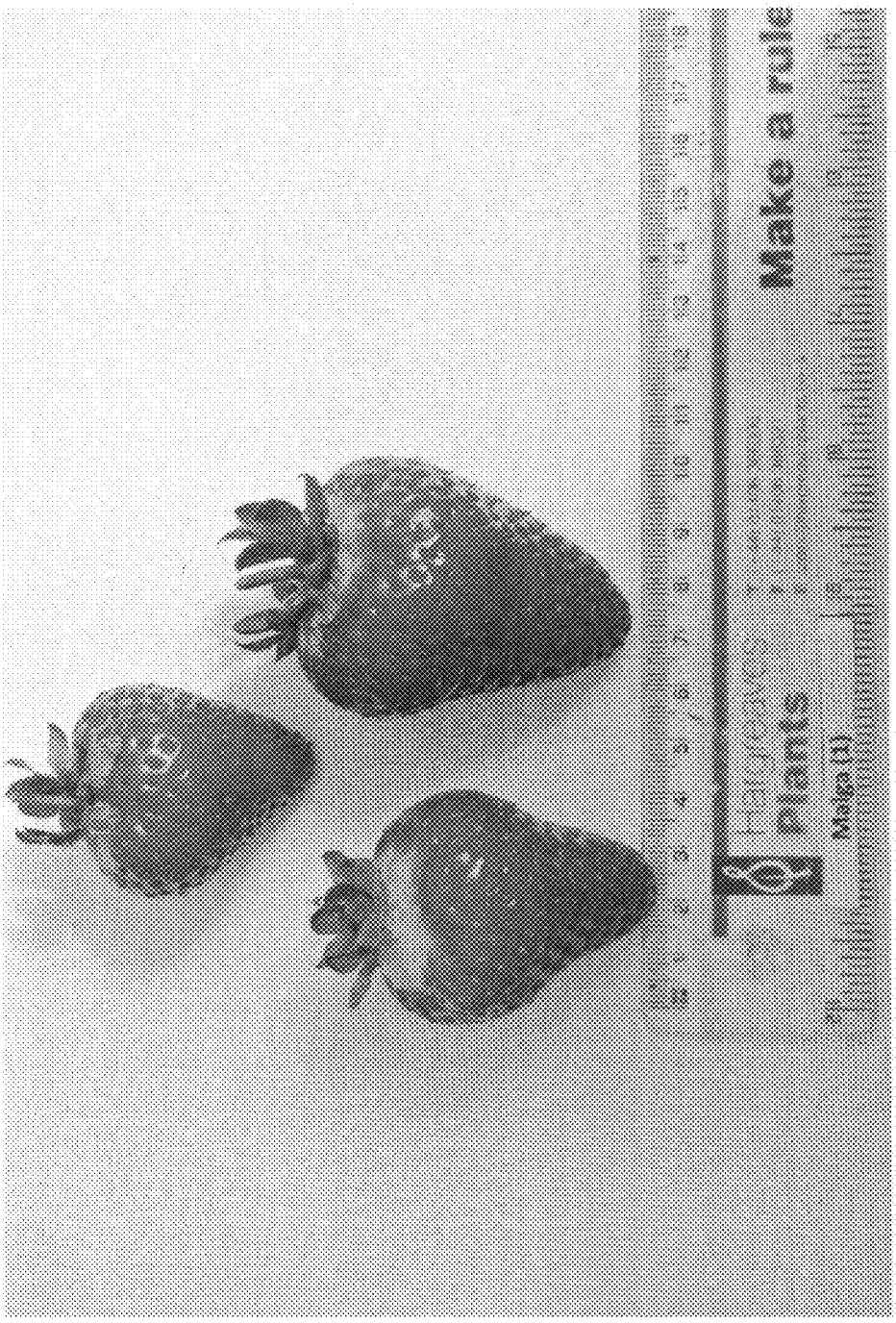

FIG. 2: illustrates close up of the fruit.

Figure 3:
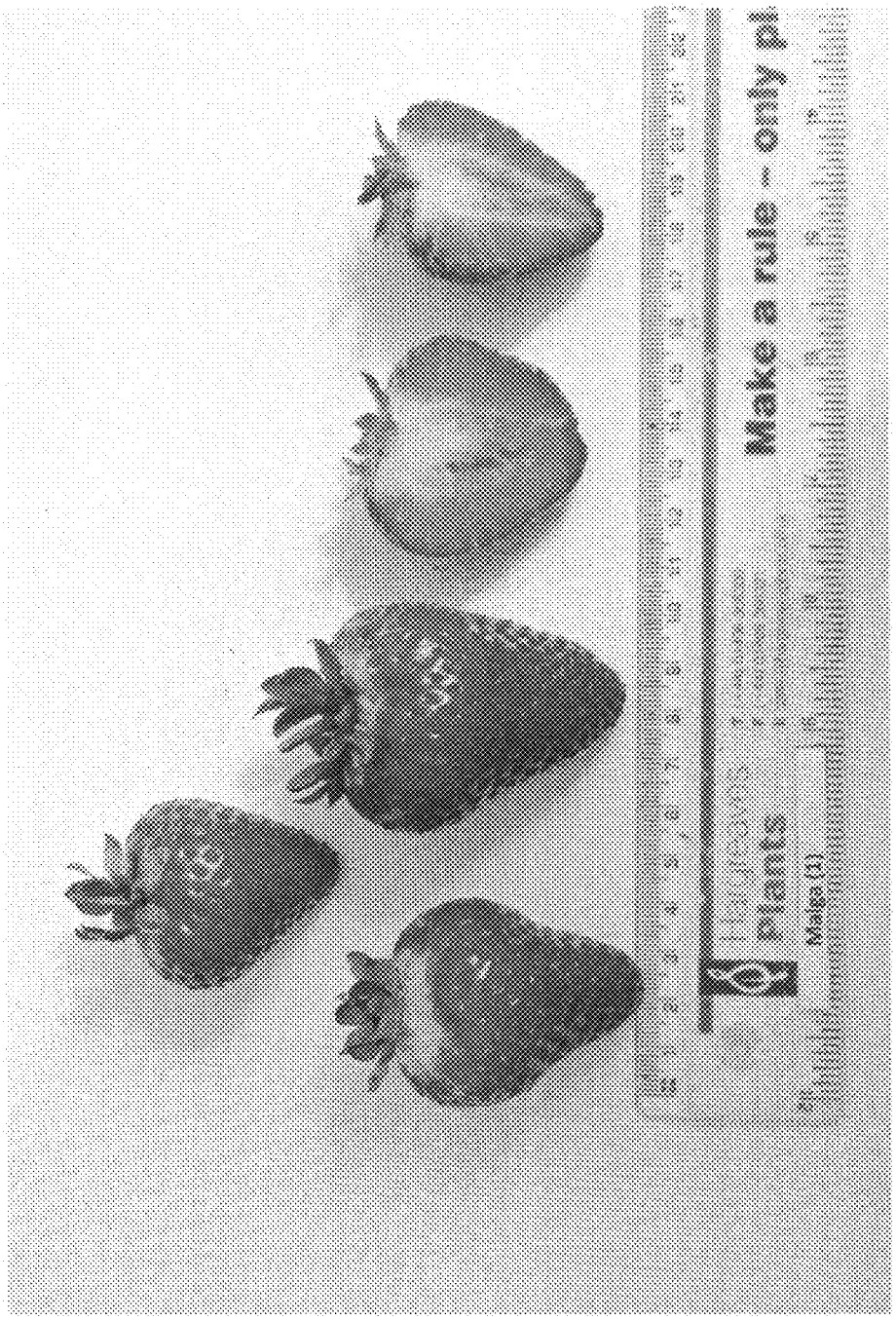

FIG. 3: illustrate close up of the fruit, including a cross section.

Figure 4:
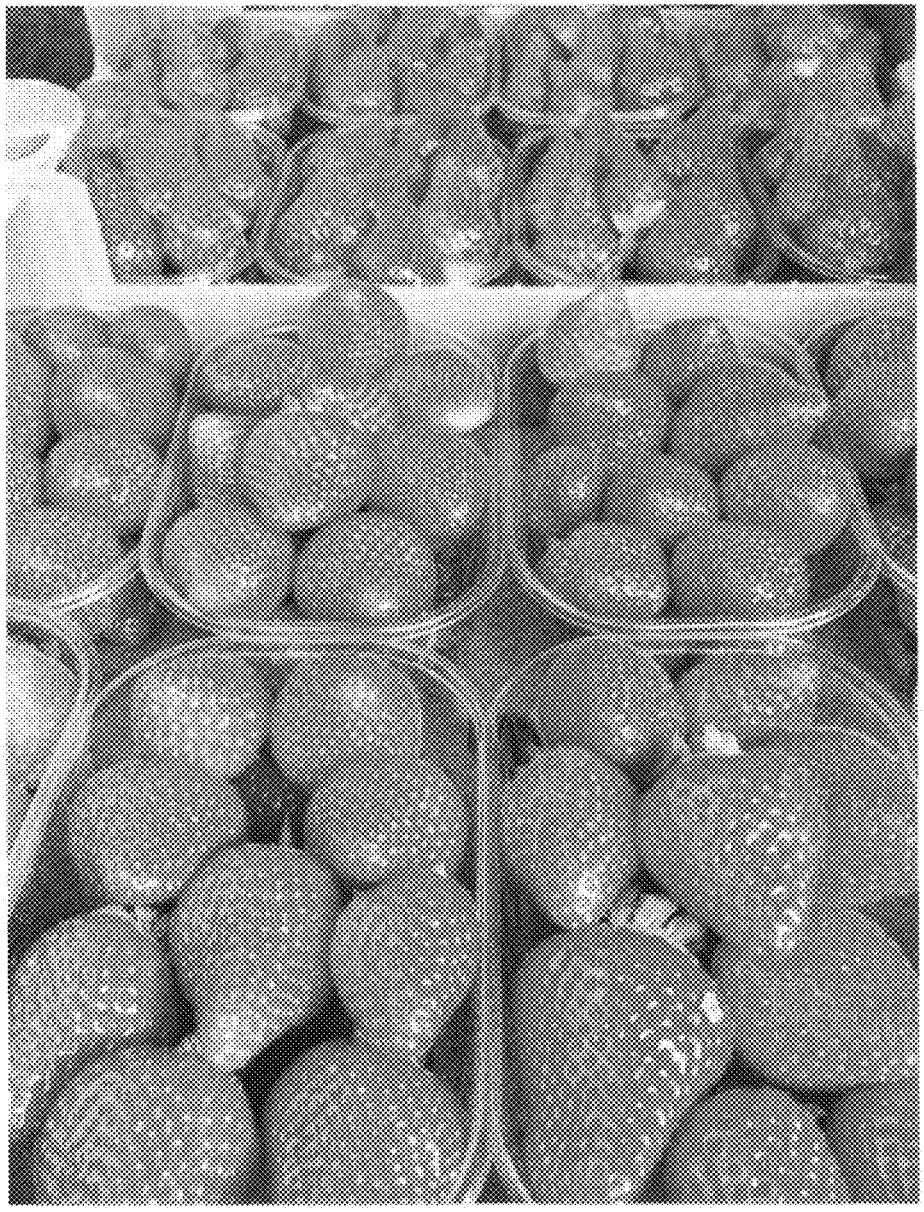

FIG. 4: illustrates commercial size baskets of fruit, with approximately 100 fruits total, exhibiting consistency of size and shape.

Figure 5:
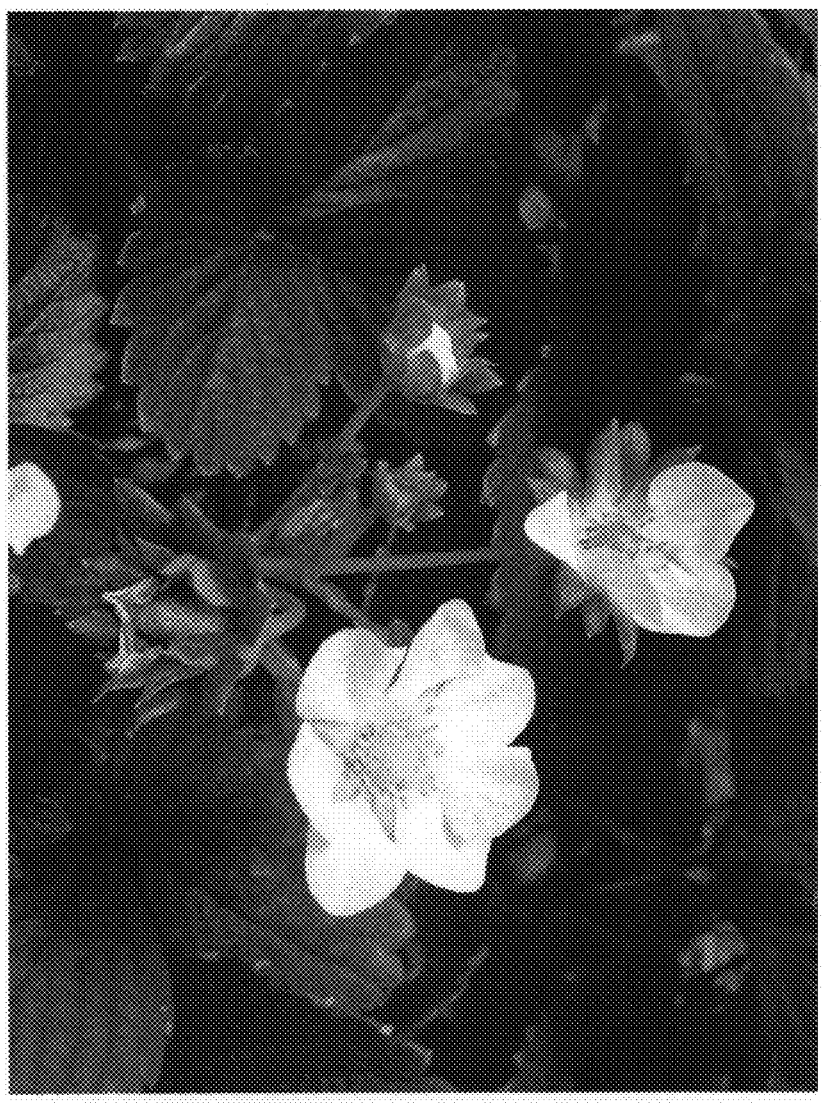

FIG. 5 illustrates a close up of the flower.

DETAILED BOTANICAL DESCRIPTION

In the following description, color references are made to The Royal Horticultural Society Colour Chart 2007 except where general terms of ordinary dictionary significance are used. The following observations and measurements describe 'MALGA' plants grown in the Summer of 2014, in open sided poly tunnels Sutton Bridge, Lincolnshire, United Kingdom. Plants were grown on table tops with substrate bags of buffered coco peat. No chemical treatments, including growth regulators were given. The growing temperature ranged from 10° C. to 26° C. during the day and from 6° C. to 10° C. during the night. General light conditions are bright, normal sunlight. Measurements and numerical values represent averages of typical plant types.

Botanical classification: *Fragaria* 'MALGA'.

Propagation:
- *Type of propagation typically used.*—Bareroot plants.
- *Root description.*—Densely fibrous Plant:
- *Age of plant described.*—Approximately 6 to 8 months.
- *Average crowns per plant.*—5.
- *Plant spread.*—36.6 cm.
- *Plant height.*—19 cm.
- *Habit.*—Upright.
- *Density of individual plant.*—Medium density.
- *Quantity of stolons.*—6-8 per plant.

Stolon:
- *Diameter.*—0.331 cm, after 6 months.
- *Texture.*—Smooth, non-pubescent.
- *Color.*—Near RHS Yellow-Green 1149A and 149B.

Foliage:

Leaf:
- *Arrangement.*—Opposite.

Leaf:
- *Type.*—Typically a compound leaf with 3 leaflets.

Leaflets:
- *Average length.*—5.91 cm. Range between 5.25-6.28 cm.
- *Average width.*—4.74 cm. Range between 4.06-5.29 cm.
- *Shape of blade.*—Deltoid.
- *Aspect.*—Concave.
- *Apex.*—Acute.
- *Base.*—Rounded.
- *Attachment.*—Stalked.
- *Margin.*—Serrate to Crenate.
- *Blistering.*—Weak.
- *Appearance and texture of top surface.*—Slightly glossy, glabrous.
- *Appearance and texture of underside.*—Glabrous, matte.
- *Color.*—Mature foliage upper side: Near RHS Green N137 D. Mature foliage under side: Near RHS Green N138 C.

Petiole:
- *Length.*—1.11 cm.
- *Diameter.*—0.57 cm.
- *Pubescence.*—Small quantity of pubescence on adaxial surface. Hairs upward.
- *Color.*—Near RHS Yellow-Green 145 C.

Petiolule:
- *Color.*—Near RHS Yellow-Green 149A and 149B, colors present individually.

Stipule:
- *Stipule length.*—30.85 mm.
- *Stipule diameter.*—19.07 mm.

Flower:

Individual flowers:
- *Type.*—Single, rotate flowers.
- *Position held on plant.*—Above foliage.
- *Diameter.*—2.9 cm.
- *Depth.*—1.8 cm.
- *Bloom time.*—Plants begin flowering approximately first week of May, with last flowering around September. Flowering is not day length dependent.

Petals:
- *Quantity.*—10.
- *Length.*—13.4 mm.
- *Width.*—11.89 mm.
- *Shape.*—Reniform.
- *Spacing.*—Overlapping.
- *Color.*—Upper Surface: Near RHS White NN155B. Lower Surface: Near RHS White NN155B.
- *Texture.*—Smooth and soft.
- *Margin.*—Entire.
- *Apex.*—Rounded, blunt.
- *Base.*—Blunt.
- *Size.*—Length: 1.34 cm. Width: 1.19 cm.
- *Stigma color.*—Near RHS Yellow 6B.
- *Style color.*—Near RHS Yellow 6B.
- *Anther color.*—Near RHS Yellow-Orange 14B.
- *Filament color.*—Near RHS Yellow-Green 150D.

Pedicel:
- *Length.*—3.5 to 8.5 cm.
- *Diameter.*—3 mm.
- *Color.*—Near RHS Green 137B.
- *Texture.*—Pubescent, hairs upward.

Fruit:
- *Predominant general shape.*—Long, conical.
- *Variance in fruit shape between primary and secondary fruits.*—None.
- *Length.*—Avg. 5.16 cm.
- *Width.*—Avg. 4.28 cm.
- *Average typical quantity of berries per plant.*—27.
- *Texture or evenness of fruit surface.*—Smooth and glossy.
- *Interior flesh color when ripe.*—Near RHS Orange-Red N30B.
- *Evenness of flesh color.*—Moderately even and consistently colored.
- *Exterior surface color when ripe, exterior.*—Top: Near RHS Yellow-Green 150B. Side: Near RHS Red 44A.

*Achene color*.—Near RHS Red 46A.
*Achene quantity*.—Medium.
*Achene position*.—Below skin surface.
*Band without achenes*.—Approximately 4 to 8 mm.
*Calyx insertion*.—Upright.
*Calyx attachment*.—Slightly raised.
*Size of calyx in relation to fruit*.—One tenth the length of the fruit.
*Color of calyx*.—Near RHS Green 137 A and 137B, both colors present individually.
*Ease of calyx removal*.—Medium.
*Firmness of flesh*.—Fairly firm (498.8 g/N).
*Brix at harvest*.—7.3.
*Average weight*.—26.8 grams.
*Minimum weight*.—22.4 grams.
*Maximum weight*.—27.2 grams.
*Fruit peduncle length*.—68.47 mm.
*Fruit peduncle diameter*.—3.35 mm.
*Fruit peduncle color*.—Near RHS Yellow-Green 145B.
*Harvest time*.—First harvest: Third week of May, in the United Kingdom, research harvest. Last harvest: Second seed of June, in the United Kingdom, research harvest. Overall cropping quantity: 711.9 g/plant.

OTHER CHARACTERISTICS

Storage life: Storage life is a minimum of 6 days at 3 degrees C.
Disease/pest resistance: Neither resistance nor susceptibility to normal diseases and pests of *Fragaria* have been observed to date.
Temperature tolerance: Extreme temperature tolerance not yet observed. Plants have been successfully grown under test conditions in the United Kingdom and Northern Italy.

What is claimed is:

1. A new and distinct cultivar of *Fragaria* plant named 'MALGA' as herein illustrated and described.

* * * * *